(12) United States Patent
Canty et al.

(10) Patent No.: US 7,446,869 B2
(45) Date of Patent: Nov. 4, 2008

(54) GRANULAR PRODUCT INSPECTION DEVICE

(75) Inventors: Thomas M. Canty, Williamsville, NY (US); Paul J. O'Brien, East Aurora, NY (US); Christian P. Marks, Cheektowaga, NY (US); Richard E. Owen, Youngstown, NY (US)

(73) Assignee: J.M. Canty Inc., Buffalo, NY (US)

( * ) Notice: Subject to any disclaimer, the term of this patent is extended or adjusted under 35 U.S.C. 154(b) by 280 days.

(21) Appl. No.: 11/315,779

(22) Filed: Dec. 21, 2005

(65) Prior Publication Data

US 2006/0221338 A1 Oct. 5, 2006

Related U.S. Application Data

(63) Continuation-in-part of application No. 10/400,723, filed on Mar. 27, 2003, now Pat. No. 7,009,703.

(51) Int. Cl.
*G01N 15/02* (2006.01)

(52) U.S. Cl. ...................... 356/335; 356/445

(58) Field of Classification Search ......... 356/335–343, 356/237.1, 445–448; 382/110, 141; 250/573, 250/574
See application file for complete search history.

(56) References Cited

U.S. PATENT DOCUMENTS

| | | | | |
|---|---|---|---|---|
| 3,655,964 A | * | 4/1972 | Slight ........................... | 378/53 |
| 4,194,634 A | * | 3/1980 | Kelly .......................... | 209/589 |
| 4,252,240 A | * | 2/1981 | Satake ......................... | 209/580 |
| 4,365,719 A | * | 12/1982 | Kelly .......................... | 209/589 |
| 5,101,101 A | * | 3/1992 | Sawamura .............. | 250/223 R |
| 5,135,114 A | * | 8/1992 | Satake et al. ................. | 209/558 |
| 5,413,222 A | * | 5/1995 | Holder ........................ | 209/567 |
| 6,629,010 B2 | * | 9/2003 | Lieber et al. ................. | 700/109 |
| 7,016,043 B2 | * | 3/2006 | Fukumori et al. ............ | 356/432 |
| 2004/0189991 A1 | | 9/2004 | Canty et al. .................. | 356/335 |
| 2006/0055934 A1 | * | 3/2006 | Sunshine et al. ............ | 356/446 |

FOREIGN PATENT DOCUMENTS

JP 8-161454 * 6/1996

\* cited by examiner

*Primary Examiner*—Hoa Q Pham
(74) *Attorney, Agent, or Firm*—Darby & Darby

(57) ABSTRACT

A particle inspection device includes a feeder configured to drop a particle through an image area. The feeder includes a tray surface having a flat portion and an edge portion disposed above the image area. The inspection device also includes a vibration device configured to vibrate the feeder induce movement of the particle from the flat portion to the edge portion and an image capturing device configured to capture an image of the particle in the image area. The edge portion may be a downwardly curved edge section and configured to maintain the orientation and reduce tumbling motion as the particle slides off the tray and falls through the image area. Alternately or additionally, a landing element is provided having a landing surface disposed in the image area and angled with respect to the flat portion of the tray surface and configured to receive the particle. The image capturing device is configured to capture an image of the particle on the landing surface.

13 Claims, 6 Drawing Sheets

GRANULAR PRODUCT INSPECTION DEVICE

RELATED APPLICATIONS

This application is a continuation-in-part of U.S. patent application Ser. No. 10/400,723, filed on Mar. 27, 2003, now U.S. Pat. No. 7,009,703 the entire disclosure of which is hereby incorporated by reference herein.

BACKGROUND OF THE INVENTION

The present invention relates generally to inspection systems and particularly to a method and device for inspecting of particles.

It is often desirable to inspect particles that are produced or created during various industrial processes. Inspection may be useful for determining properties of the particles, including, for example, size, shape, purity, surface roughness, color, and uniformity. The particles may be inspected for a variety of reasons, for example, as part of a quality control process, for sorting, or for identifying particular qualities of the particles including defects.

Several devices and methods are known for inspecting and analyzing particles. For example, many such methods and devices employ laser diffraction, spectroscopy, and various forms of visual image analysis.

One known image analysis technique of particle inspection captures a two-dimensional image of particles being inspected as they fall from a feeder through an image area. The captured image is analyzed using software running on a microprocessor to determine certain properties of the particles, such as size and shape. For non-spherical particles, for example, rock fragments and particles produced in mining and aggregate industries, analysis of a two-dimensional image can lead to an incorrect determination of the true size or shape of the particle.

One known inspection system uses three-dimensional image analysis to inspect the shape of coarse aggregates. That known system relies on the analysis of two separate images taken at right angles from two separate cameras of aggregate particles moving on a conveyor belt. The use of separate cameras and separate images has several disadvantages including additional cost of the inspection device as well problems in calibrating the two separate images. In addition, obtaining high image quality of particles as they are being transported on a conveyor belt can be problematic and can diminish the accuracy and precision of the particle observations and/or measurements.

SUMMARY OF THE INVENTION

An object of the present invention is to provide a method and device for inspection of particles in an efficient and cost effective manner. A further object of the present invention is to provide a method and device that presents particles for inspection in an advantageous way for capturing high quality images of the particles.

The present invention provides a particle inspection device that includes a feeder configured to drop a particle through an image area, wherein the feeder includes a tray surface having a flat portion and a downwardly curved edge portion disposed above the image area, a vibration device configured to vibrate the feeder so as to induce movement of the particle from the flat portion to the downwardly curved edge portion, and an image capturing device configured to capture an image of the particle in the image area. When capturing an image of a particle falling through the image area, the downwardly curved edge portion helps to minimize tumbling or rotation of the particle as it falls, particularly when oblong-shaped particles are being inspected. Because the particles tend to settle on the vibrating feeder with their largest faces facing the tray surface, the curved edge surface tends to rotate the major face of the particle as the particle slides along the curved surface so that when the particle falls, the major face is aligned perpendicularly with the camera during its fall. This allows the view of the camera to obtain the largest possible circumference of the particle.

The particle inspection device may also include a first light source disposed opposite the image capturing device and configured to provide backlighting of the particle for the image, and or a second light source configured to provide front lighting of the particle for the image. The flat portion may be disposed at a slight angle from the horizontal so as to encourage movement of the particle from the flat portion to the downwardly curved edge portion when the feeder is vibrated.

The downwardly curved edge portion preferably includes a first section tangential to the flat portion and a second section tangential to a drop angle of the particle and may define a radius of curvature that is larger than a minimum thickness of the particle. Preferably, the downwardly curved edge portion is configured to enable the particles to slide off the edge of the tray without inducing a rotational movement to the particles.

The particle inspection device may also include an image processing device in operative connection with the image capturing device and configured to determine a property of the particle, such as a size property, a shape property, a color property, and/or a surface roughness property. The image capturing device defines a sighting axis and may be disposed such that the sighting axis is substantially perpendicular to the drop angle of the particle and preferably at an angle from horizontal.

The present invention also provides a method for inspecting a particle, that includes providing a feeder having a tray surface that includes a flat portion and a downwardly curved edge portion, disposing the particle on the flat portion, vibrating the feeder so as to induce movement of the particle from the flat portion to the downwardly curved edge portion, sliding the particle over the downwardly curved edge portion and dropping the particle from the downwardly curved edge portion through an image area, and capturing an image of the particle in the image area using an image capturing device.

Furthermore, the present invention provides a particle inspection device that include a feeder configured to drop a particle through an image area, wherein the feeder includes a tray surface having a flat portion and an edge portion disposed above the image area, a vibration device configured to vibrate the feeder so as to jog the particle from the flat portion to the edge portion, a landing element having a landing surface disposed in the image area and configured to receive the particle, a relative landing angle between the landing surface and the flat portion of the tray being less than 90 degrees, and an image capturing device configured to capture an image of the particle on the landing surface. The landing element is preferably configures to receive the falling particles at an angle so that particle slides down the landing surface with the major face of the particle facing toward the landing surface and at a perpendicular angle to a view of the camera.

Preferably, the relative landing angle is greater than 30 degrees. The flat portion of the tray surface should be disposed at a slight angle from the horizontal so as to encourage movement of the particle from the flat portion to the edge portion when the feeder is vibrated. The edge portion may be advantageously curved downwardly from the flat portion toward an edge of the tray. The image capturing device defines a sighting axis and may be disposed so that a relative sighting angle between the sighting axis and the landing surface is perpendicular.

The landing element may be pivotably mounted relative to the feeder so that the relative landing angle is adjustable about a pivot point. A relative distance between the pivot point and the tray surface may be adjustable. A camera mount may be provided and connected at a fixed angle to the landing device. The image capturing device may be mounted on the camera mount so that a relative sighting angle between the sighting axis and the landing surface is unchanged during an adjustment of the landing angle.

The landing surface may be transparent and a first light source may be disposed behind the landing surface so as to provide backlighting of the particle for the image. The first light may be a back panel light disposed directly adjacent to the landing surface. A second light may be additionally provided and configured to provide front lighting of the particle of the image. A color of the landing device may be chosen to contrast with a color of at least one portion of the particle.

The present invention furthermore provides a method for inspecting a particle. The method includes providing a feeder having a tray surface that includes a flat portion and an edge portion, disposing the particle on the flat portion, vibrating the feeder so as to induce movement of the particle from the flat portion to the edge portion and dropping the particle from the edge portion through an image area, receiving the particle on a landing surface disposed in the image area at an angle less than 90 degrees from the flat tray surface, and capturing an image of the particle on the landing surface using an image capturing device.

The feeder preferably includes a tray surface angled downward toward a first end of the feeder disposed above the image area and the particle inspection device preferably also includes a vibration device configured to jog the particle toward the first end of the feeder. The first end of the feeder may advantageously include a downwardly curved edge portion. A first section of the curved edge portion is preferably tangential to the tray surface, and a second section of the curved edge portion is preferably tangential to a drop angle of the particle. The curved portion of the end of the feeder is preferably shaped so as to encourage a translation of the particle and to discourage a rotation of the particle, so that the particle slides off the end of the tray with minimal rotational movement as it falls. If the end of the tray ends abruptly, with no curved transition surface, the particles, particularly oblong-shaped particles, will tend to tumble as they fall through the image area. If the particle is tumbling during its free-fall through the image area, the orientation of the particle with respect to the image capturing device is not well-controlled, and is unlikely to include a principal face of the particle. Particularly when inspecting particles having elongated shapes, it is desirable to have at least one view that shows a principle face of the particle. As the particle vibrates along the tray surface, it will tend to settle in a position such that its principal face is facing downwards against the tray surface. When the particle reaches the curved edge portion, it will tend to slide along the curved edge portion with the principal face facing the surface of the curved edge portion. Thus, as the particle slides down the curved edge surface, the principle face is slowly being rotated so as to be facing the image capturing device as it falls from the end of the curved edge portion and through the image area.

The method may be performed on a particle having a major diameter between 50 microns and 6000 microns, and/or on a particle has a major diameter between 0.1 inches and 3.0 inches, and/or on a particle having a major diameter greater than 1 inch.

BRIEF DESCRIPTION OF THE DRAWINGS

The present invention will be discussed in the following with reference to the drawings, in which.

DETAILED DESCRIPTION

Figure 1:
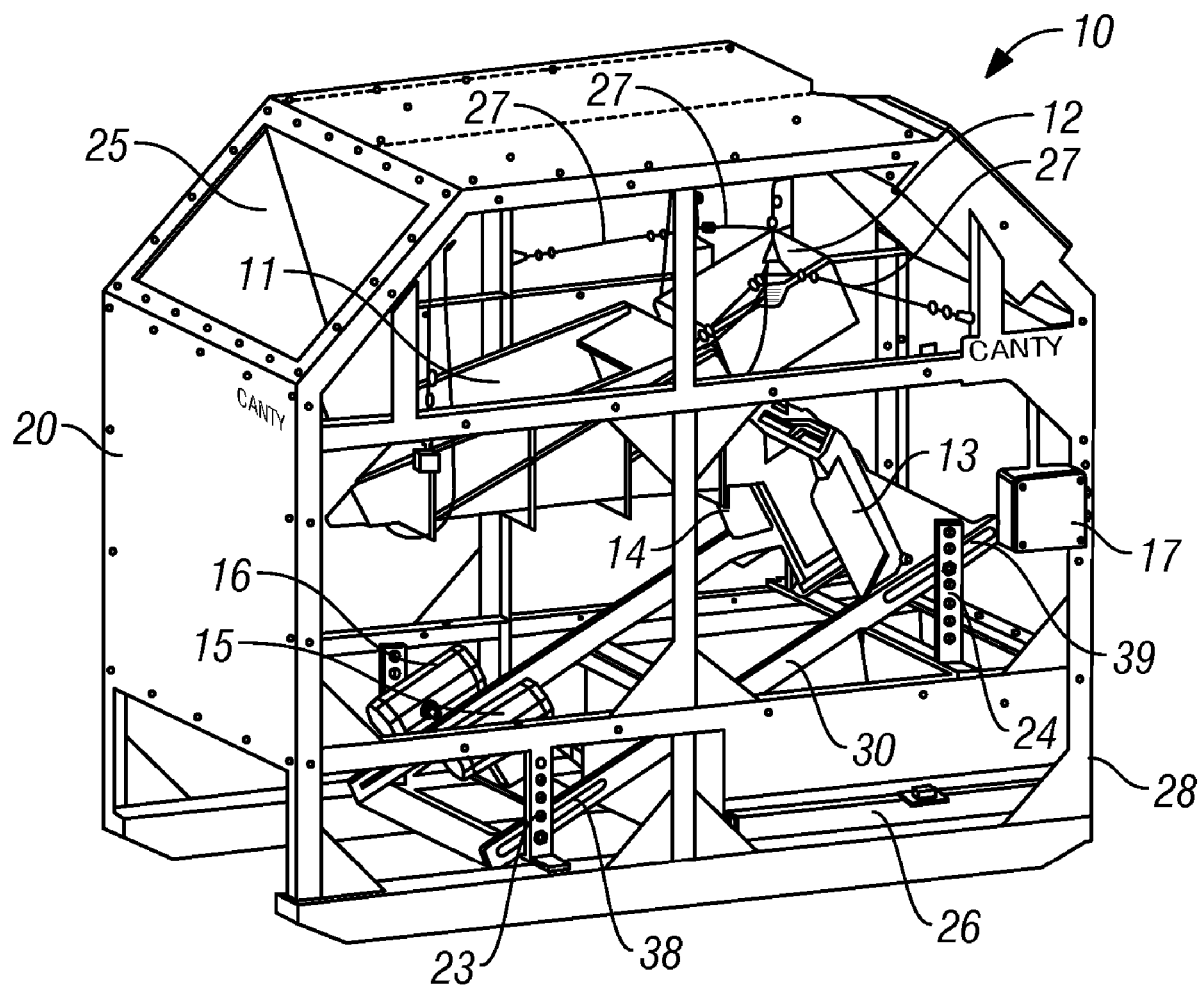
FIG. 1 shows a perspective view of a particle inspection device according to the present invention.

FIG. 1 shows a perspective view of one embodiment of a particle inspection device 10, which includes housing 20. Inside the housing, a feeder 11 is suspended from the housing using mounting cables 27. A vibration device 12 is rigidly connected to the feeder 11 and also suspended from the housing 10 using mounting cables 27. A particle inlet opening 25 enables particles to be placed into the feeder 11. In a laboratory setting, a user of the device may place a sample of particles to be inspected through the particle inlet opening 25. Alternatively, the device could be used in-line so that the particles flow through the opening from a previous process operation.

The feeder includes a tray surface that is preferably slightly inclined downward from the end proximate the particle inlet opening 25. When particles are in the feeder 11 and the vibration device 12 is switched on, such as by switching on switch 17, the feeder is vibrated by vibration device 12, which jostles the particles so that they may migrate toward the downward end of the feeder 11, which is adjacent the vibration device 12 in FIG. 1. When the particles reach the downward end of the feeder, the particles fall into catch tray 26. The particles can be removed from the housing through opening 28 in the rear of the housing by the device user. Alternatively, if the inspection device were to be used in-line with a larger production or inspection process, the particles could fall into a chute or otherwise flow to a subsequent process operation. An imaging assembly 30 is mounted to supports 23 and 24, which each include a plurality of holes, using bolts passing through slots 38 and 39 respectively, of imaging assembly 30. In this way, the imaging assembly 30 is mounted in a manner such that its position and angle can be adjusted to provide optimal viewing and imaging conditions.

Figure 2:
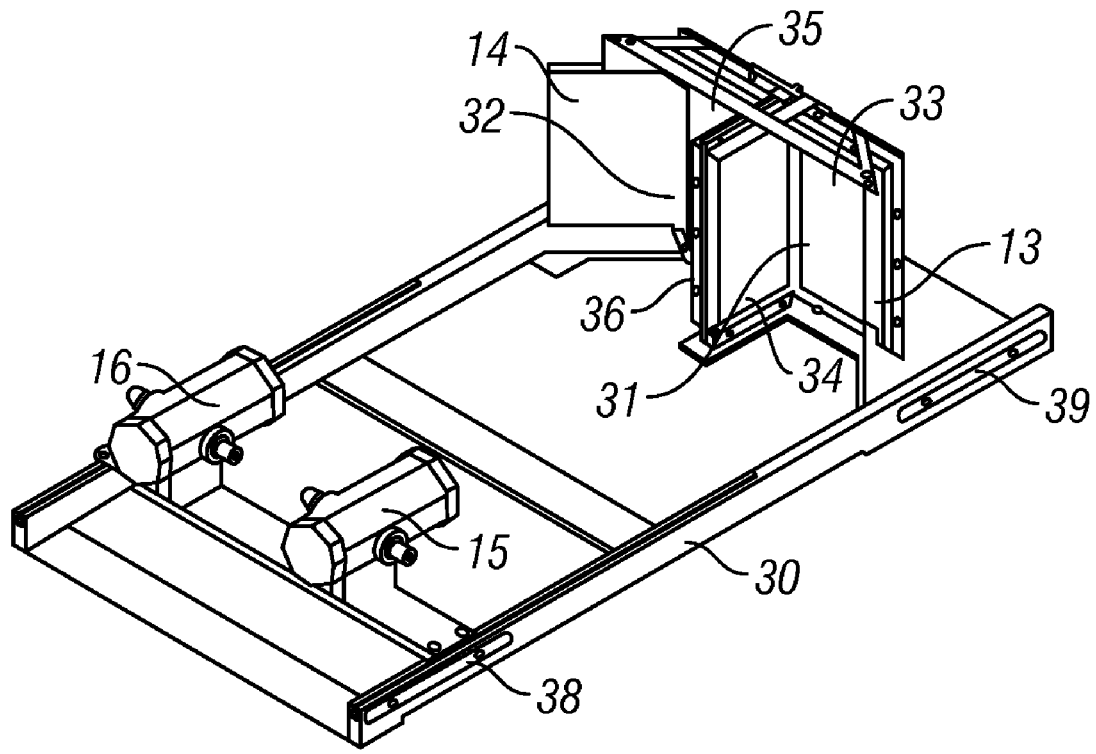
FIG. 2 shows a perspective view of the imaging assembly of the particle inspection device shown in FIG. 1.

Imaging assembly 30 is shown in more detail in FIG. 2. Two image capturing devices, for example CCD cameras 15 and 16, are mounted at one end of imaging assembly 30. At an opposite end, an illumination panel 33 is mounted opposite camera 15 and illumination panel 35 is mounted opposite camera 16. Image area 31 includes the area in front of illumination panel 33 through which particles fall from the feeder 11 to the catch tray 26. A second image area 32 includes the area in front of illumination panel 35 through which particles fall from the feeder 11 to the catch tray 26. Because the particles fall between a camera and illumination pair (15 and 33, or 16 and 35, respectively), the illumination panels 33 and 35, when illuminated, provide backlighting for a direct view of the particles from cameras 15 and 16, respectively. LED panels may be used as the illumination panels.

Although the embodiment shown includes a pair image capturing devices 15, 16 and a pair image areas 31, 32, this is not necessary for the functioning of the invention. An imaging assembly including a single image capturing device 15 and single image area 31 would work as well. The use of two cameras merely increases the rate at which particles can be inspected as two images can be captured of different particles and simultaneously processed.

In addition, imaging assembly 30 includes reflector 13, such as a mirror, which is positioned within a field of view of the first image capturing device 15 such that it provides a reflected side view of particles falling through the image area 31 to image capturing device 15. Illuminated panel 34, which is oriented 90 degrees with respect to illumination panel 33, provides backlighting to the reflected side view taken from camera 15. Similarly, reflector 14 is positioned within the field of view of second camera 16 such that it provides a reflected side view of particles falling through the second image area 32 to second camera 16. Illuminated panel 36, which is oriented 90 degrees with respect to illumination panel 35 (and back-to-back with respect to illumination panel 34) provides backlighting to the reflected side view taken from camera 16.

Figure 3:
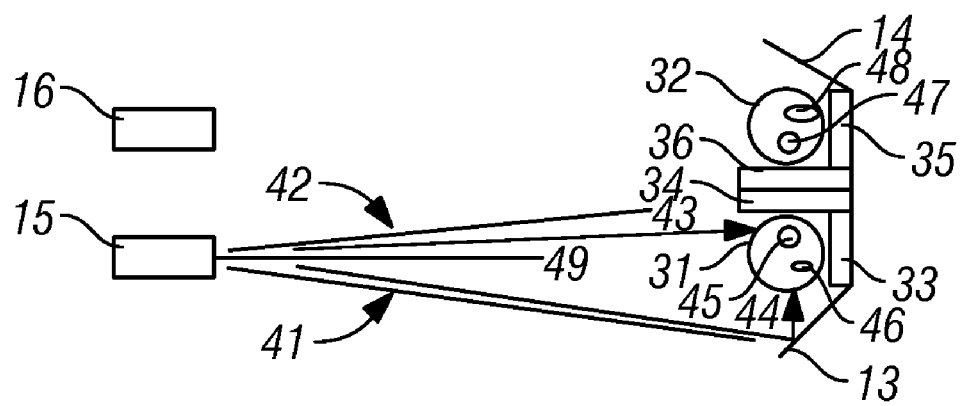
FIG. 3 shows a schematic view of a portion of the imaging assembly shown in FIG. 2.

FIG. 3 shows a schematic view of the components of the imaging assembly 30. Particles 45 and 46 are shown falling within first image area 31. Particles 47 and 48 are shown falling within second image area 32. First camera 15 defines sighting axis 49 and a field of view between boundary lines 41 and 42. The direct view 43 of the image area 31 taken from camera 15 is shown schematically by arrow 43 and the reflected side view taken from camera 15 is shown schematically by arrow 44.

Figure 4:
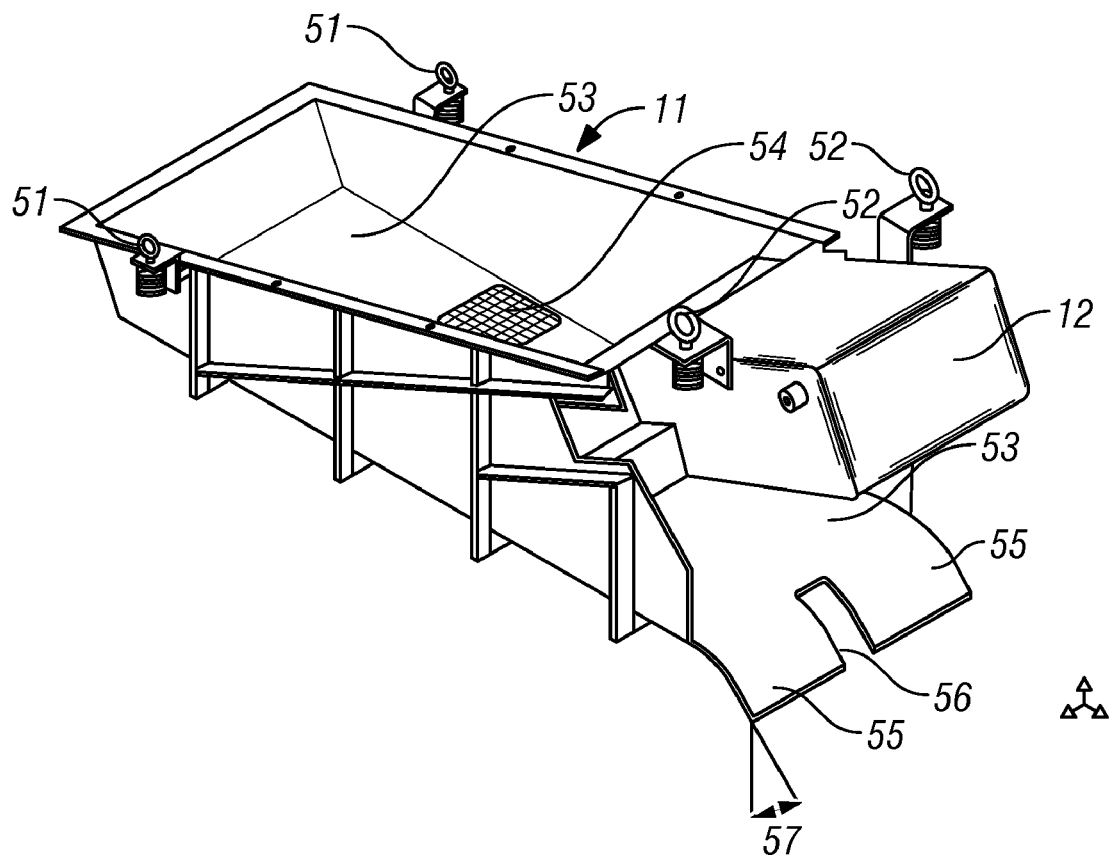
FIG. 4 shows a perspective view of the feeder and vibration device of the particle inspection device shown in FIG. 1.

The feeder 11 and vibration device 12 are shown in more detail in FIG. 4. Feeder 11 includes two mounting elements 51. Feeder 11 is rigidly attached to vibration device 12, which also includes two mounting elements 52. Mounting elements 51 and 52 each including a loop connected to a spring. Mounting cables 27 are connect to the loops of mounting elements 51 and 52 in order to suspend the feeder 11 and the vibration device 12 from the housing. The springs in mounting elements 51 and 52 provide damping action in order to smooth out the vibrations to feeder 11 and to allow a smoother migration of the particles from one end of the feeder to the other. Feeder 11 includes tray surface 53 at its bottom. Feeder is preferably disposed within housing 20 in such a manner that tray surface 53 slopes downward slightly toward the open end of the feed tray (disposed underneath vibration device 12 in FIG. 4). The slight downward slope coupled with the vibrations induces a migration of the particles from one end of the feeder to the other.

At its open end, tray surface 53 includes downwardly curved portion 55. Curved portion 55 provides a smooth transition to the particles as they fall off the edge of tray surface 53 and helps to orient the particles so that a principle surface of the particle is directed toward the camera during free-fall through the image area. Through the vibration of the feeder 11, the particles, which may include rock fragments or other particles having oblong shapes, will tend to settle into a position with their principle face (i.e. the face having the largest substantially flat surface area) downward. If the tray surface were to include an abrupt edge without a downwardly curved edge portion, the oblong-shaped particles would tend to tumble off the edge of the feeder and rotate end-over-end as they fell through the image area. In effect, the edge would act to flip the trailing edge upward as the leading edge of the particle began to fall. With the curved edge portion 55, the particles will tend to slide down the edge portion with their principle faces adjacent to the surface of the curved edge portion 55. Thus, as the particles slide down the curved edge portion, they become oriented such that their principal faces are facing toward image capturing device and in a direction perpendicular to the direction of movement of the particle as it begins to fall from the feeder. The end of the curvature of edge portion 55 is preferably tangential with the initial angle of fall 57 of the particle from feeder 11. In addition, imaging assembly 30 is preferably mounted within housing 20 so that the sighting axis of the camera is perpendicular to the direction of fall of the particles. In this way, the particles will tend to fall with only minimal rotational movement, if any. During the fall, the principal faces of the particles will be oriented substantially toward the camera. In this way, the direct view of the particle from the camera will show the principle face of the particle, which is useful, especially for size and shape determinations of oblong-shaped particles.

The direction of fall of the particle will typically not be directly vertical, at least not during the upper portion of its fall. Rather, as it leaves the end of curved portion 55, the particle will be sliding along in the direction of the angle 57 of the curved portion. The direction of fall will become more vertical later in the fall as gravity accelerates the particle downward. Therefore, as shown in FIG. 1, in order to capture an image of the particles perpendicular to their direction of fall through the image area, the imaging assembly 30 is typically mounted in housing 20 at an angle from direct horizontal.

Figure 7:
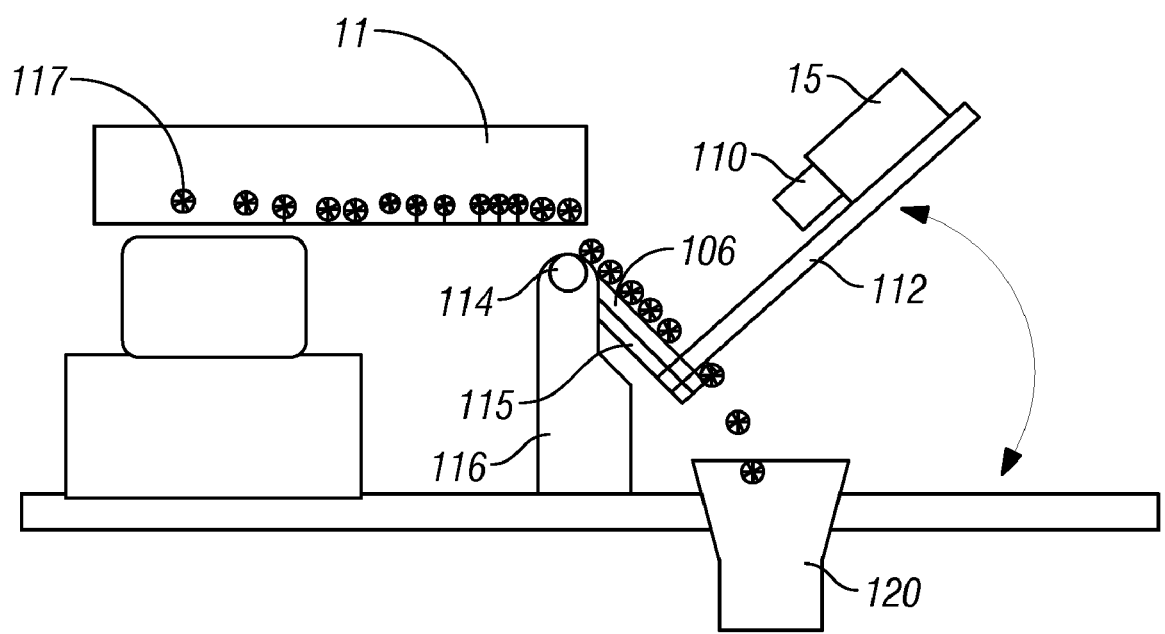
FIG. 7 shows a side view of a further second of a particle inspection device according to the present invention.
Figure 8:
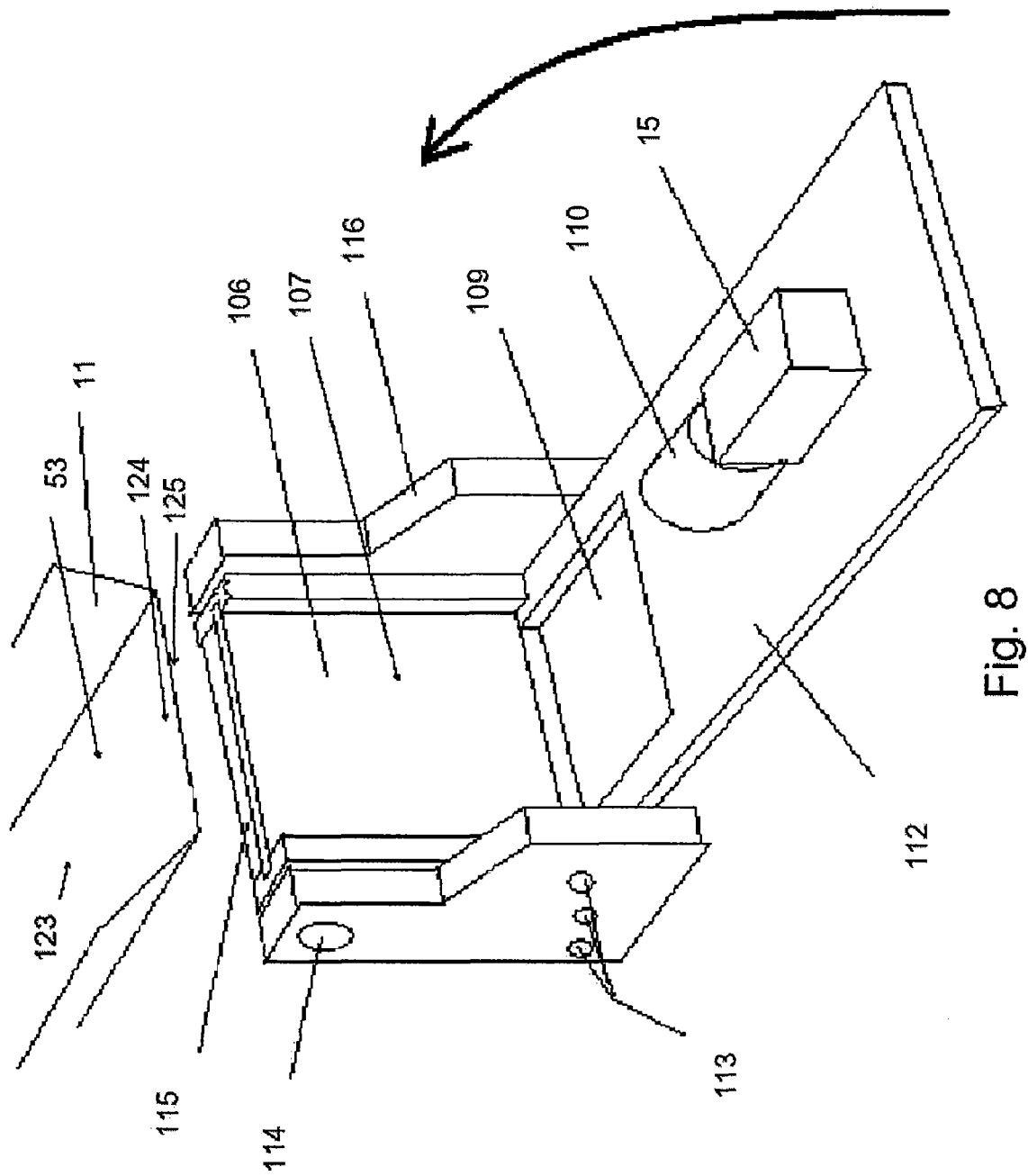
FIG. 8 shows a perspective view of the second embodiment.

One variation of the inspection device includes a landing element, which may be a landing tray 106 is shown in FIGS. 7 and 8. The landing plate 106 is an additional means of ensuring that the principal face of the particle is directed toward the camera and may work in conjunction with, or instead of, the curved edge portion 55. As shown schematically in FIGS. 7 and 8, landing plate 106 having surface 107 is disposed in the image area beneath the edge 105 of feeder 11 in a tilted orientation. Feeder 11 has a tray surface 53 that includes a flat portion 123 and an edge portion 124. The edge portion 124 may be flat and coplanar with flat portion 123 or may be downwardly curved such as curved portion 55 in FIG. 4. The use of the landing plate 106 is particularly useful for situations of two dimensional viewing (without a side view), since the landing element may interfere with a reflected view of the particles.

As shown schematically in FIGS. 7 and 8, particles 117 are moved along the feeder 11 from the flat portion 123 to the edge portion 124 until they reach edge 125, where they drop off. Landing element 106, which can be a landing plate, is disposed beneath the edge 125. Landing surface 107 of landing element 106 is tilted relative to the flat portion 123 of the tray surface 53. Preferably, the relative angle is somewhere between 30 degrees and 90 degrees and is set according to the characteristics of the particles being inspected, such as size, weight, density, and degree of bounce. Advantageously, the landing the angle of tilt is chosen so that the particles to land on the surface 107 and achieve and maintain a flat position relative to the camera 15 and lens 110 until the image is taken while the particles are still on the landing plate. The particles then slide down the landing surface 107 and fall into catch bin 120, which may later be emptied or which may feed the particles to a further processing step. As shown in FIG. 8 a recess 109 may be provided in camera mount 112 to allow the particles to pass through to the catch bin 120 after sliding off the bottom edge of landing surface 107.

Whether or not edge portion 124 is downwardly curved the landing plate assists in ensuring the optimal orientation of the falling particles for imaging. For example, depending on the characteristics of the particles being measured, some particles may be launched from the feed tray and substantially miss making contact with the curved lip of the tray. The tilted landing plate allows those particles to achieve a flat position with respect to the view of the camera.

The landing plate 106 is preferably rigidly connected to, or integral with, camera mount 112, upon which the camera 15 is mounted, at a perpendicular angle, so that the view of the camera 15 is always oriented at a perpendicular angle to the landing surface 107. The landing plate is mounted in a pivotable manner with respect to landing element support 116, such as by pivot rod 114 which defines a pivot point about which the landing plate can be pivoted. This the relative angle between the fall direction of the particles and the landing surface 107 may be adjusted according to the characteristics of the particle so as to optimize the view and minimize bounce. Locking pins 113 can be used to lock the angle of the landing plate. Because of the rigid connection between the camera mount 112 and landing plate 106, the viewing angle of the camera 15 remains the same as the relative landing angle for the particles is adjusted.

The landing element support 116 and the landing plate 106 are separated from the feeder 11 at a distance. The pivot rod 114 may be mounted on the landing rod so that at least a vertical distance between the landing surface 107 and the edge 125 of the feeder 11 can be adjusted so that the distance of the fall of the particle can be adjusted according to the particle characteristics, so as to reduce bounce on the landing surface, for example.

Preferably, conditions of background color and light are adjusted for optimal viewing. For example, backlighting may be provided by back panel light 115, wherein the landing plate 106 itself is transparent. The intensity and color of the light are preferably chosen to optimize the contrast conditions for viewing those characteristics of the particles being viewed. Front lighting may also be provided alternatively or in addition to the backlighting. A color may be selected for the landing surface to contrast optimally with a color of the particle or a color of one portion of the particle in the case of multi-colored particles. This may be performed by placing a colored panel behind the transparent landing plate or by replacing the transparent landing plate with a colored landing plate.

As shown in FIG. 4, tray surface 53 of feeder 11 may also include screened recess 54 at an intermediate portion between the two ends, which may be provided in order to remove particularly fine particles ("fines") from a particle sample being inspected. In some instances, the volume of fines that are mixed with the larger particles can create a "dirt curtain" through the image area, or otherwise interfere with optimal imaging of the larger particles. Depending on the type of particles being inspected, and the type of analysis being performed, the gage of the screened recess may be adjusted or a feeder without a screened recess may be used.

Figure 6:
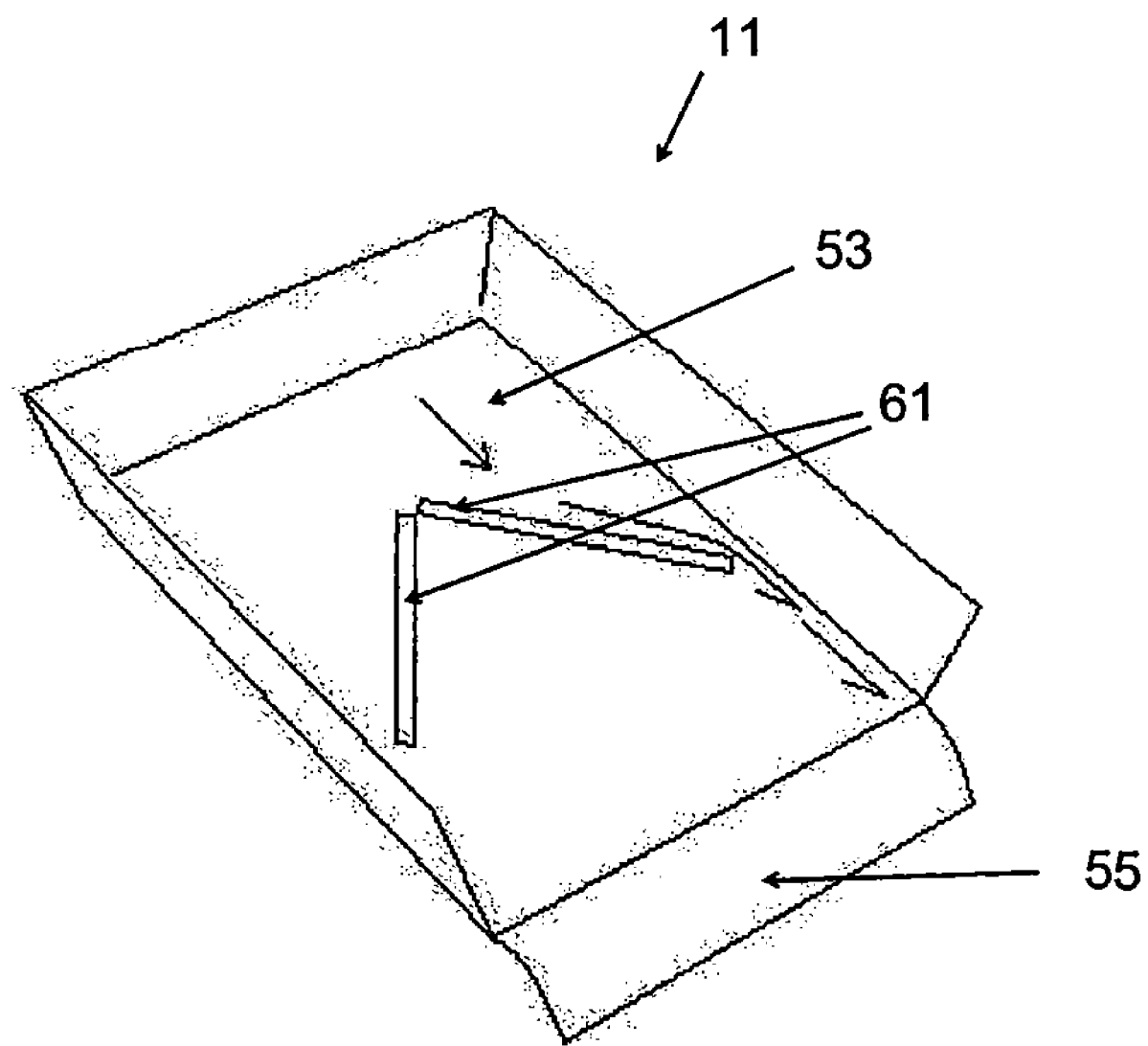
FIG. 6 show a perspective view of an exemplary embodiment of a gate mechanism.

A gating mechanism may be optionally used in the feeder with or without a screened recess to separate out particles according to size and/or to control the rate of migration of the particles through the feeder. One example of a gating mechanism, shown in FIG. 6, includes a low-profile raised portion 61 of tray surface 53 of the feeder. Raised portion 61 may be a strip of material connected, for example by welding, to tray surface 53. Raised portion 61 is sized so as to extend above the rest of surface 53 enough to divert fine particles toward the edges of tray surface 53 while enabling larger particles to vibrate over raised portion 61 without being significantly diverted. By diverting the fines to the edges of the tray surface 53, interference with the imaging of the larger particles is reduced or eliminated. The optimal height of raised portion 61 for diverting fine particles will depend on, among other factors, the size of particles being imaged and the size of fine particles to be diverted.

For applications in which the fines are an important component of the measurement, the fines can be extracted from the main flow, for example by using the screened recess 54, and sent down a chute so as to pass through a supplemental image area. A supplemental image capturing device may capture images of the fines and send them to the processor for inclusion in the total analysis of the sample. Flow of fines through a supplemental image area may be viewed with backlighting and/or using a reflector as are the particles through the first and second image areas 31 and 32.

Figure 5:
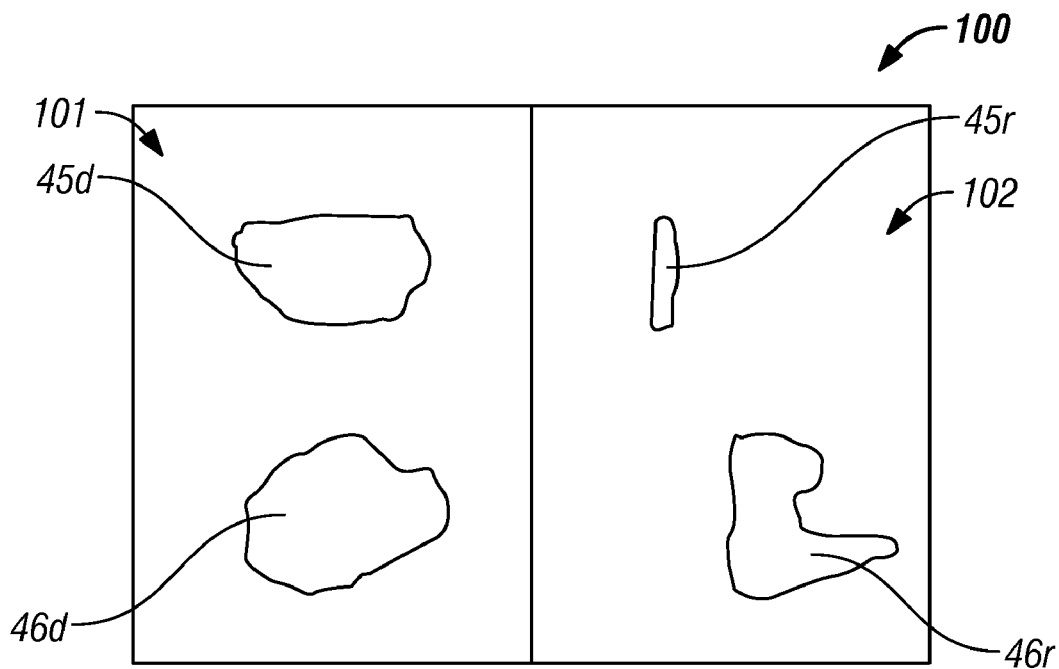
FIG. 5 shows a schematic view of an image captured from the particle inspection device shown in FIG. 1.

An example of an image 100 of particles 45 and 46 (as shown in FIG. 3) is shown in schematic form in FIG. 5. The left half of the image 100 shows a direct view 101 of image area 31 and the right half of the image shows a reflected view 102 of image area 31. 45d represents a direct view of particle 45 and 45r represents a reflected side view of particle 45. Likewise, 46d represents a direct view and 46r represents a reflected side view of particle 46. As can be seen from two views of the image, particle 45 has a rather flat shape with considerably less thickness than particle 46. The image 100, shows an example of the importance of the additional information shown in the reflected side view, especially in determining size or volume of the particles. For example, if only the direct view of the particles were available, the particle 46 may be judged to be only slightly larger than particle 45. When both views are available, it becomes clear that the volume of particle 46 is substantially greater than the volume of particle 45.

In the preceding specification, the invention has been described with reference to a specific exemplary embodiment thereof. It will, however, be evident that various modifications and changes may be made thereto without departing from the broader spirit and scope of the invention as set forth in the claims that follow. The specification and drawings are accordingly to be regarded in an illustrative rather than a restrictive sense.

What is claimed is:

1. A particle inspection device comprising:
   a feeder configured to drop a particle through an image area, wherein the feeder includes a tray surface having a flat portion and a downwardly curved edge portion disposed above the image area so that the particle falls from the downwardly curved edge portion through the image area;
   a vibration device configured to vibrate the feeder so as to induce movement of the particle from the flat portion to the downwardly curved edge portion; and
   an image capturing device configured to capture an image of the particle falling through the image area, wherein the downwardly curved edge portion includes a first section tangential with the flat portion and a second section tangential with a drop angle of the particle.

2. The particle inspection device as recited in claim 1, further comprising a first light source disposed opposite the image capturing device and configured to provide backlighting of the particle for the image.

3. The particle inspection device as recited in claim 1, further comprising a second light source configured to provide front lighting of the particle for the image.

4. The particle inspection device as recited in claim 1, wherein the flat portion is disposed at a slight angle from the horizontal so as to encourage movement of the particle from the flat portion to the downwardly curved edge portion when the feeder is vibrated.

5. The particle inspection device as recited in claim 1, wherein the downwardly curved edge portion includes a radius of curvature that is larger than a minimum thickness of the particle.

6. The particle inspection device as recited in claim 1, wherein the downwardly curved edge portion is configured to enable the particles to slide off the edge of the tray without inducing a rotational movement to the particles.

7. The particle inspection device as recited in claim 1, further comprising an image processing device in operative connection with the image capturing device, the image processing device configured to determine a property of the particle.

8. The particle inspection device as recited in claim 7, wherein the property includes at least one of a size property, a shape property, a color property, and a surface roughness property.

9. The particle inspection device as recited in claim 1, wherein the image capturing device defines a sighting axis and is disposed such that the sighting axis is substantially perpendicular to the drop angle of the particle.

10. The particle inspection device as recited in claim 9, wherein the image capturing device is disposed so that the sighting axis is oriented at an angle from horizontal.

11. A method for inspecting a particle, the method comprising:
providing a feeder having a tray surface that includes a flat portion and a downwardly curved edge portion;
disposing the particle on the flat portion;
vibrating the feeder so as to induce movement of the particle from the flat portion to the downwardly curved edge portion;
sliding the particle over the downwardly curved edge portion and dropping the particle from the downwardly curved edge portion so that the particle falls through an image area; and
capturing an image of the particle falling through the image area using an image capturing device, wherein the downwardly curved edge portion includes a first section tangential with the tray surface and a second section tangential with a drop angle of the particle.

12. The method as recited in claim 11, further comprising analyzing the image so as to determine a property of the particle.

13. The method as recited in claim 11, wherein the analyzing is performed using a microprocessor.

* * * * *